United States Patent [19]

Alderson et al.

[11] Patent Number: 4,781,548
[45] Date of Patent: Nov. 1, 1988

[54] INFUSION PUMP SYSTEM AND CONDUIT THEREFOR

[76] Inventors: Richard K. Alderson, 4525 E. Nancy La., Phoenix, Ariz. 85040; Ronald D. Sleater, 302 E. El Caminito Dr., Phoenix, Ariz. 85020; James R. Talley, 102 Oak Cir., Monroe, La. 71203

[21] Appl. No.: 36,639

[22] Filed: Apr. 10, 1987

[51] Int. Cl.$^4$ .................. A61M 5/00; F04B 43/08
[52] U.S. Cl. .................. 417/474; 417/478; 604/153; 604/251
[58] Field of Search ............ 417/474, 475, 476, 477, 417/478; 604/153, 251

[56] References Cited

U.S. PATENT DOCUMENTS

| | | | |
|---|---|---|---|
| 2,105,200 | 1/1938 | Phelps | 128/230 |
| 2,351,828 | 6/1944 | Marsh | 103/148 |
| 2,412,397 | 12/1946 | Harper | 417/474 |
| 2,689,530 | 9/1954 | Harvey | 417/474 |
| 3,658,445 | 4/1972 | Pulman et al. | 417/474 |
| 3,690,318 | 9/1972 | Gorsuch | 128/214 E |
| 3,877,428 | 4/1975 | Seagle et al. | 128/214 R |
| 4,042,153 | 8/1977 | Callahan et al. | 222/207 |
| 4,131,399 | 12/1978 | Calvert | 417/477 |
| 4,199,307 | 4/1980 | Jassawalla | 417/474 |
| 4,236,880 | 12/1980 | Archibald | 417/478 |
| 4,265,241 | 5/1981 | Portner et al. | 128/260 |
| 4,273,121 | 6/1981 | Jassawalla | 128/214 F |
| 4,277,226 | 7/1981 | Archibald | 417/38 |
| 4,398,908 | 8/1983 | Siposs | 417/474 X |
| 4,410,322 | 10/1983 | Archibald | 604/153 |
| 4,479,761 | 10/1984 | Bilstad et al. | 417/395 |
| 4,479,797 | 10/1984 | Kobayashi et al. | 604/153 |
| 4,650,469 | 3/1987 | Berg et al. | 417/474 X |
| 4,653,987 | 3/1987 | Tsuji et al. | 417/474 X |

Primary Examiner—Carlton R. Croyle
Assistant Examiner—Theodore Olds
Attorney, Agent, or Firm—Shlesinger, Arkwright & Garvey

[57] ABSTRACT

A modular infusion pump system utilizes a positive displacement pump for pumping a known quantity of fluid for each stroke. A plurality of longitudinally spaced apart fixed combs cooperate with a resilient tube to define a known pumping volume. A plurality of movable combs are interdigitated with the fixed combs and are periodically linearly directed to cause the pump volume to be compressed, and therefore the fluid expelled. A rotary to linear drive system is connected with the movable combs and a ratchet system prevents counterrotation when the motor is in the off position. Valves are disposed above and below the pumping unit to appropriately seal off the pumping volume. The valves and the movable combs are operated by means of cams carried by a common shaft.

19 Claims, 5 Drawing Sheets

INFUSION PUMP SYSTEM AND CONDUIT THEREFOR

BACKGROUND OF THE INVENTION

Proper treatment of a patient frequently requires that a particular medicament be introduced into the body in liquid form. Continuous infusion is preferred when it is desired that the concentration be substantially constant or otherwise appropriately controlled over a given length of time. This control may be effected through a metering valve or, in certain cases, through the use of a pump. Regardless of how control is attempted, it has not been possible with prior art devices to provide accurate control over the delivery of essentially all of the large number of medicaments now in use. For this reason, a great number of infusion systems have been developed, each primarily directed towards infusion of a particular medicament.

The simplest infusion system involves a metering valve downstream of a conventional intravenous (I.V.) fluid containing container. These I.V. containers are usually attached to a support stand so that the fluid flows under gravity condition through an inclined ramp metering valve. Unfortunately, these simple systems cannot maintain constant drip rate, are cumbersome and substantially prevent ambulation of the patient, and the valves do not adequately respond to changes, such as volume changes, patient changes and the like.

Various types of pumps have also been utilized in an attempt to provide accurate infusion over a given period of time. The most common type of pump involves peristaltic action. We have found that peristaltic action is itself subject to certain difficulties because of the rolling nature of the wave, as well as the inability to accurately control the pumped volume.

As noted, each particular medicament must usually be infused with a pump system specifically designed therefor, such that a large number of infusion systems are required in a modern hospital complex. The large number of infusion pumps required may allow mistakes to occur due to the unfamiliarity of the attendant personnel with the particular pump. Naturally, each infusion pump has its own settings, connections and the like, thereby greatly increasing the amount of information which the attendant personnel must possess to adequately utilize these systems. Training of the attendant personnel is thereby complicated and only serves to increase total hospital costs.

Hospitals have recently been under great pressure to minimize costs. The ever increasing number of infusion systems only serves to increase costs, thereby adding to consumer complaints. Ambulation of the patient is one means for shortening the hospital stay, thereby one means for decreasing patient costs.

The disclosed invention is an infusion pump system and conduit which is designed to replace the large number of infusion systems presently known. The disclosed invention includes a modular infusion pump which is extremely lightweight, thereby permitting ready ambulation by the patient. Furthermore, the invention is battery powered, thereby cutting the tether to the A/C power supply system. Lastly, the disclosed invention is a positive displacement volumetric pump which operates on a known pumping volume, thereby assuring accurate delivery and includes a brake assembly to prevent reverse infusion as can occur in prior art pumps.

OBJECTS AND SUMMARY OF THE INVENTION

The primary object is an infusion pump system which is lightweight, portable and capable of use with the infinite number of medicaments now requiring separate infusion systems.

The infusion pump system of the invention is operable on a resilient longitudinal tube to cause a medicament to be pumped therethrough. A plurality of fixed spaced apart first combs define a contoured surface for receiving the tube. A door closing the system housing positions the tube into engagement with the first combs and maintains the tube there so that a known pumping volume is achieved. A plurality of movable spaced apart second combs are interdigitated with the first combs for reciprocally compressing the pumping volume for causing fluid to be selectively expelled therefrom, or drawn thereinto. Valves are positioned upstream and downstream of the pumping volume for selectively closing and opening the tube to permit fluid flow to or from the pumping volume. A rotary drive system includes a rotary to linear conversion device which displaces the second combs and the valves for causing selective operation thereof. A brake is connected with the rotary drive system for preventing unintended rotation thereof, and thereby prevents unintended movement of the second combs such as could cause fluid to be siphoned back into the pumping volume.

The disclosed invention is a positive displacement volumetric infusion pump. The pump has a high degree of accuracy per pumping cycle. The pumping tube has an oblong shape conforming to the contoured configuration of the fixed combs in order to achieve a fixed reference volume and, because of the shape, requires less force for compression, thereby saving battery power. The pump may automatically purge itself of air through appropriate manipulation of the valves. Furthermore, a one way brake prevents back slippage and permits the motor to be turned off after each cycle, so that the motor remains off during the majority of the time.

The disclosed infusion pump has a unique pumping chamber and a high efficiency pumping system that is self-priming and purges air from the delivered fluid. The positive displacement volumetric pump delivers a precise volume during each stroke. The system provides universal service for all pressure and gravity administered tasks. The invention replaces the prior art peristaltic roller pumps, syringes, transfer diaphrams, plunger systems and the like.

A microprocessor controls the pump mechanism and has a video display to permit all appropriate parameters to be set, as well as to display selected operating parameters as may be required. The pump is programmed with the help of "lead-through" prompts, thereby assuring that all pertinent information is input for proper operation, and also lessening the information which the attendant personnel must remember.

These and other objects and advantages of the invention will be readily apparent in view of the following description and drawings of the above described invention.

DESCRIPTION OF THE DRAWINGS

The above and other objects and advantages and novel features of the present invention will become apparent from the following detailed description of the preferred embodiment of the invention illustrated in the accompanying drawings, wherein.

DESCRIPTION OF THE INVENTION

Figure 1:
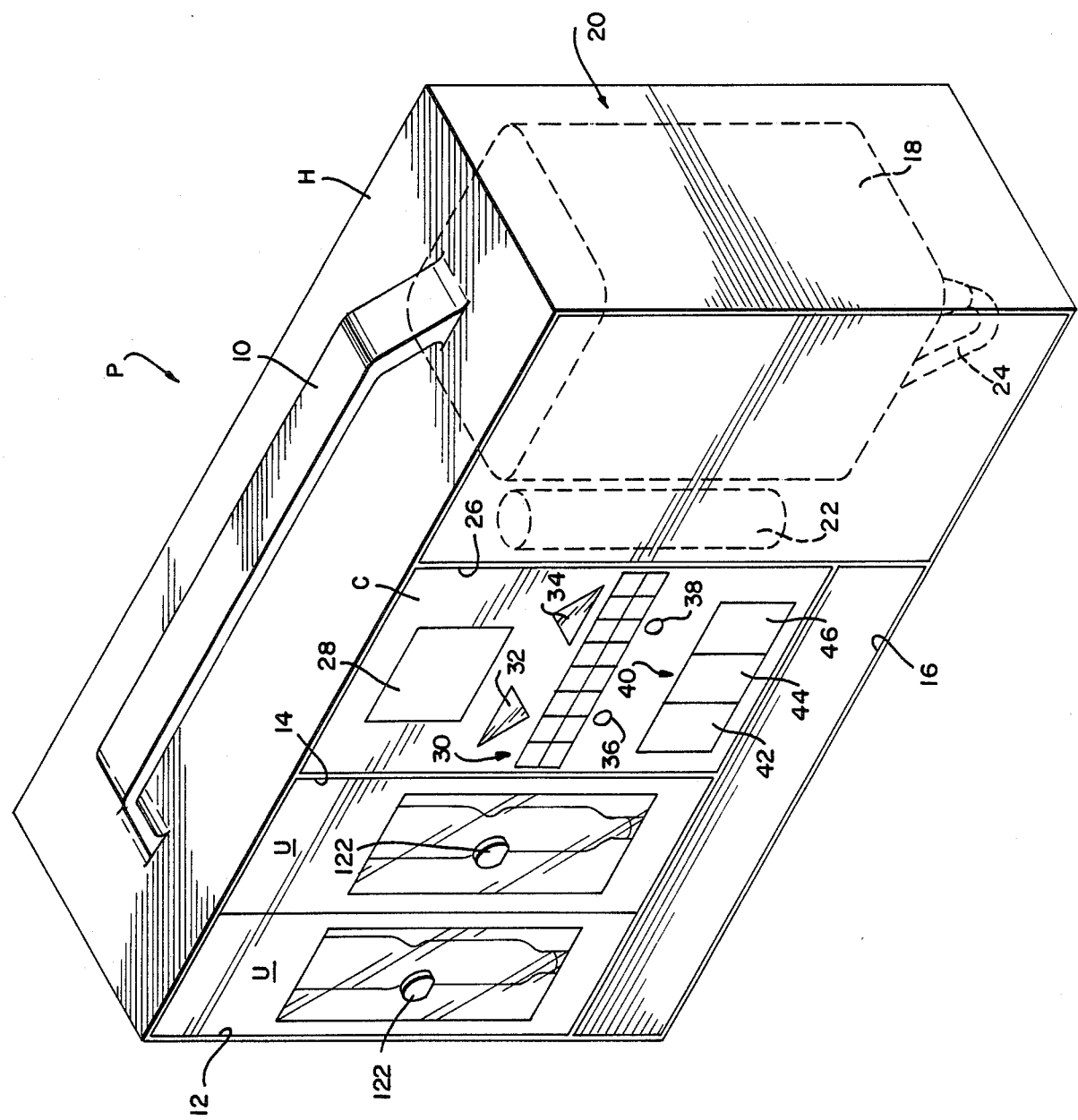
FIG. 1 is a perspective view illustrating the infusion system of the invention.
Figure 2:
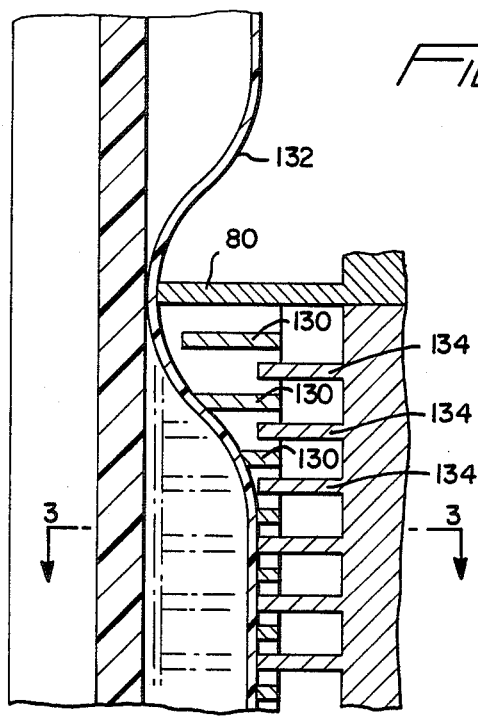
FIG. 2 is a fragmentary cross-sectional view illustrating the pumping system of the invention.

Infusion pump system P, as best shown in FIG. 1, is contained within housing H. The housing H is, preferably, manufactured from a high strength plastic or similar lightweight material in order to permit the pump system P to be readily carried by the patient (not shown). Preferably, housing H has a carrying handle 10 extending along the top surface. The housing H, along with its related ancillary items, weighs approximately 2.5 pounds, this including the weight of the batteries which provide the operating power.

Housing H has a first chamber 12 extending along a sidewall thereof and in which a first modular pump unit U, as will be further described, is positioned. A second chamber 14 is disposed adjacent first chamber 12 and likewise receives a pump unit U. Chamber 12 preferably contains a piggyback pump unit which pumps a secondary medicament which is contained within lower chamber 16. The primary medicament is contained within medicament bottle 18 positioned within side housing 20. A syringe 22 may be advantageously positioned within housing 20 for use by the patient as needed. FIG. 1 also discloses medicament supply line 24 which is in flow communication with primary pump unit U of chamber 14.

Control unit C is contained within chamber 26 of housing H and is used for setting the operating parameters, as well as for monitoring the operating parameters of the individual pump units U.

Control unit C, as best shown in FIG. 1, includes a video display 28 and programming push buttons 30. The control unit C also includes indicator lights 32 and 34 which let the operator know if the particular parameter of interest is being raised or lowered Similarly, indicating lights 36 and 38 are provided to indicate a hold function, as well as an alarm mode, respectively. Lastly, control unit C includes a programming module 40 to allow the operator to select which of the pumping units U is to be displayed or adjusted. As noted, the programming module 40 includes indicators 42, 44 and 46 because the pumping system P can handle as many as 3 pump units U.

Figure 8:
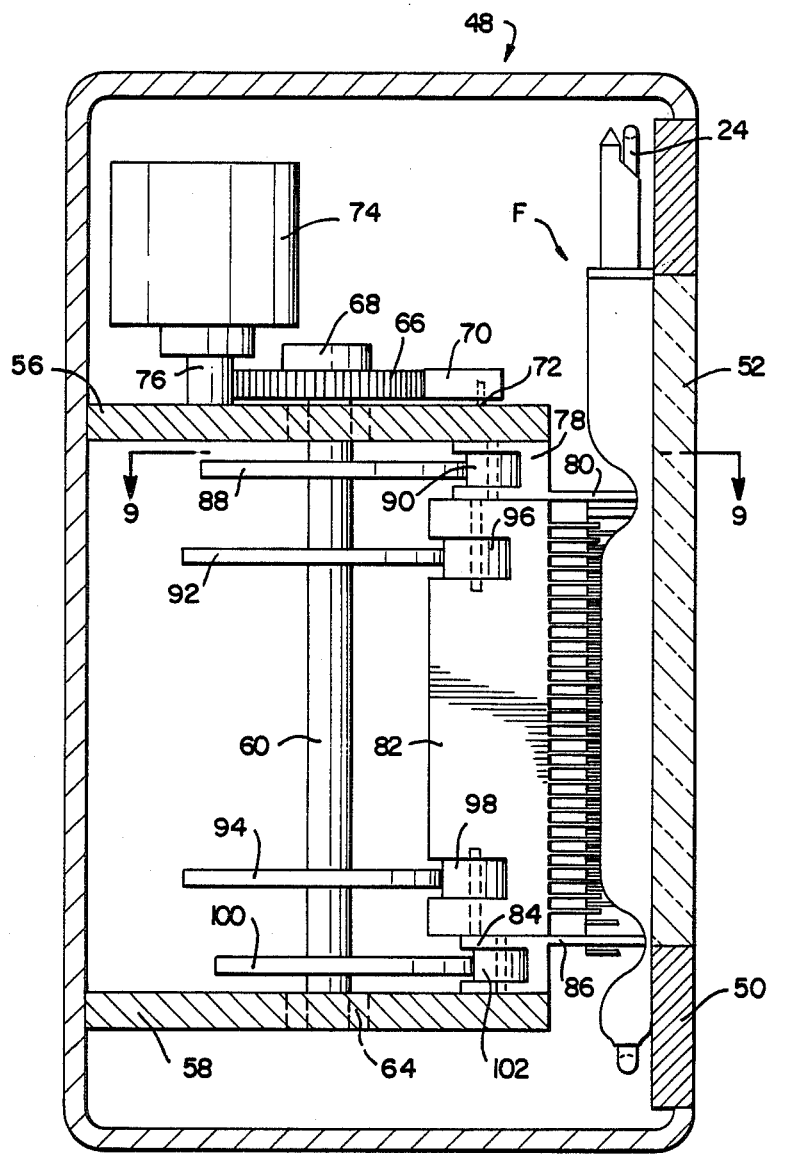
FIG. 8 is a cross-sectional view illustrating the drive system of the invention in cooperation with the administration set of FIG. 6.
Figure 9:
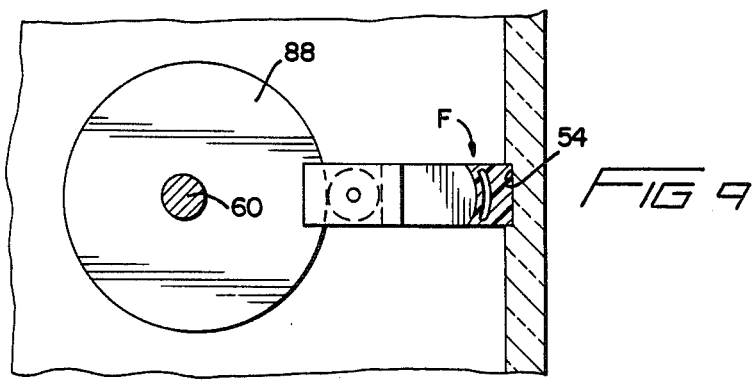
FIG. 9 is a cross-sectional view taken along the section 9—9 of FIG. 8 and viewed in the direction of the arrows; and, FIG. 10 is a schematic diagram illustrating the control circuit of the invention.

FIGS. 8 and 9 disclose the high efficiency pump mechanism which each pump unit U employs in order to provide an accurate controlled pumped volume of medicament. Each pump unit U includes a generally rectangular housing 48 having a pivotal door 50. The door 50 has a transparent window 52 to permit the operator to view fluid ducts F during use. FIG. 9 discloses recess 54 which receives and positions the duct F for operation.

An upper member 56 and a lower member 58 extend from the rear wall of housing 48 in general parallel alignment. The members 56 and 58 extend toward the door 50, although they stop short thereof. Rotatable shaft 60 extends between the members 56 and 58, and preferably is supported by bearings 62 and 64 in order to permit free rotation thereof. Driven gear 66 is carried by shaft 50 and is secured thereto by nut 68. Ratchet pawl 70 pivots on pin 72 in order to provide a brake permitting the gear 66 to rotate in one direction only.

Electric motor 74, which preferably is a direct current motor, has a rotatable shaft which carries a drive gear 76. The drive gear 76 is in meshing engagement with the driven gear 66 in order to cause rotation of same. Naturally, appropriate wiring is provided for connecting the motor 74 with the control unit C, as well as with the source of electric power, and need not be further explained.

First slidable valve 78 is carried by support member 56 and includes a contact portion 80 which is engageable with fluid duct F to compress, and thereby close, same. A pump shoe 82 is slidably disposed relative to valve 78 and likewise includes a plurality of contact portions, as will be further explained, for compressing duct F. Second valve 84 is slidably disposed relative to shoe 82 and member 58. Valve 84 has a contact portion 86 which is likewise used for compressing, and thereby closing, duct F. The valves 78 and 84 may be slidably keyed to shoe 82 and likewise to members 56 and 58, respectively or all may be positioned between parallel guide plates.

Cam 88 is carried by shaft 60 and is engageable with rotatable cam follower 90 carried by valve 78 for causing linear displacement of the valve 78.

Cams 92 and 94 are carried by shaft 60. The cams 92 and 94 are engageable with rotatable cam followers 96 and 98, respectively, carried by shoe 82 for likewise causing linear displacement of pump shoe 82. The cams 92 and 94 are spaced apart in order to prevent canting of the shoe 82 during displacement.

Cam 100 is carried by shaft 60. Cam 100 is engageable with rotatable cam follower 102 carried by valve 84 for causing linear displacement of valve 84. It should be clear that the cams 88, 92–94 and 100 are appropriately adjusted so that the nodes thereof cause selected linear displacement of the associated valves 78 and 84, respectively, as well as of pump shoe 82.

Figure 6:
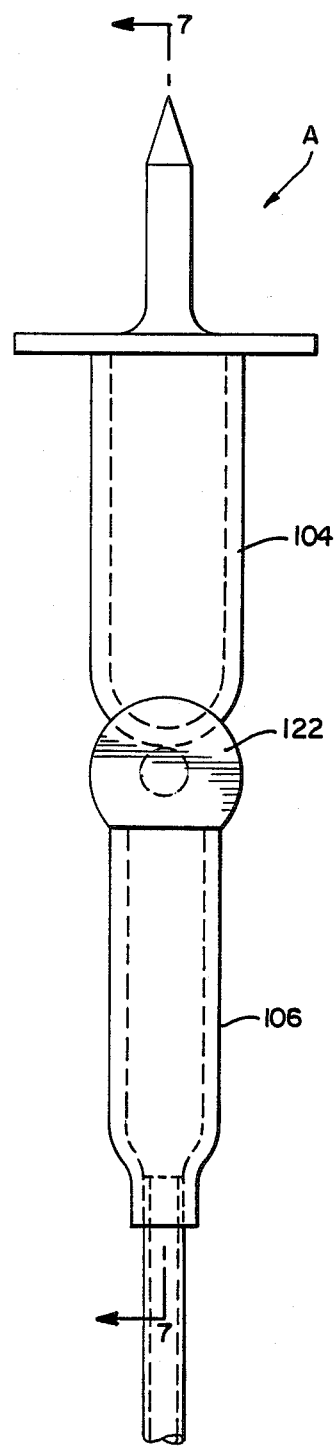
FIG. 6 is a front elevational view of the administration set of the invention.
Figure 7:
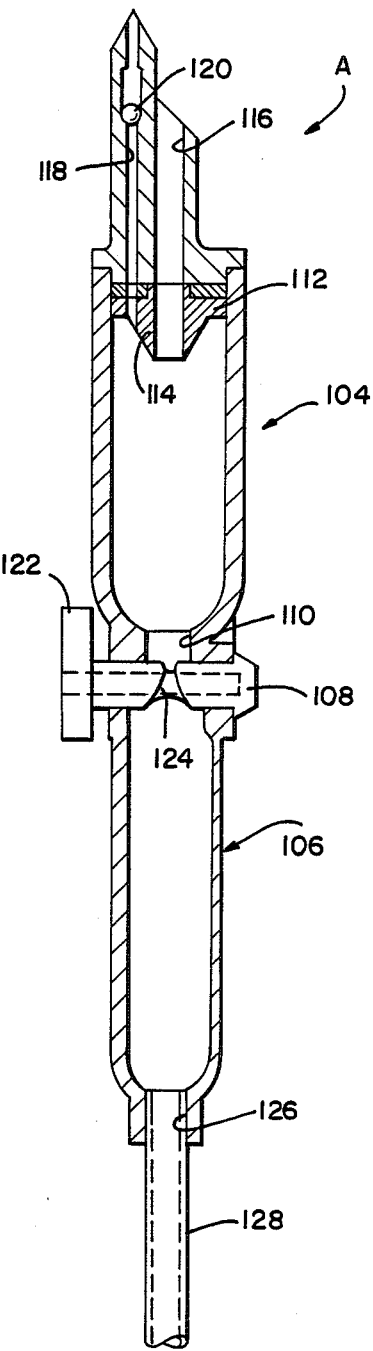
FIG. 7 is a fragmentary cross-sectional view thereof.

Administration set A is best shown in FIGS. 6 and 8 and provides the fluid duct F which is secured by the door 50. The administration set A includes an upper drip chamber 104 which is in flow communication with pump chamber 106 by means of variable orifice valve 108 disposed across duct 110. Preferably, the drip chamber 104 is integral with the pump chamber 106 and both are comprised of a resilient, preferably transparent, polymeric material, such as urethane or silicone, which is easily compressible, for reasons to be explained. Set A may be used independently of unit U as a metering valve.

Drip chamber 104 has an inlet opening 112 in which orifice 114 is received. The orifice 114 is preferably manufactured from a non-wetting material, such as Teflon, or is coated with a corresponding substance. The non-wetting material controls drop size and thereby further insures accurate delivery of the medicament to drip chamber 104. Naturally, orifice 114 has an inlet opening 116 for connection with a fluid supply source, such as hose 24 of container 18. Vent 118 communicates through orifice 114 with drip chamber 104 and includes ball check 120 to prevent entry of contaminants into the drip chamber 104 through vent 118.

Valve 108 includes a handle 122 which controls logarithmic opening 124. Rotation of handle 122 therefore provides logarithmic control over the quantity of fluid which can flow from the drip chamber 104 to the pump chamber 106. Additionally, the handle 122 may include means cooperating with the door 50 to secure same in the locked, or closed position. This assures that the valve 108 is in the off position when the unit U is initially set up, in order to prevent full flow of medicament to the patient.

Pump chamber 106 includes a circular outlet opening 126 which is connected with cannula 128. The cannula 128 is of conventional design and permits the medicament to flow to the patient much as with prior art systems.

The pumping chamber 106 will now be explained with reference to FIGS. 2-5. As noted, fluid duct F, which includes the administration set A, is secured within housing 48 by means of door 50 and window 52. The window 52 presses the fluid duct F against first fixed position combs 130. The combs 130 are fixed relative to the supports 56 and 58 and extend towards door 50 and therefore provide a contoured surface for receipt of wall portion 132 of duct F. The fixed position combs 130 encompass wall portion 132 and define a known pumping volume for the pumping chamber 106. The known pumping volume assures that a constant volume of medicament is always present at the time of initiation of the pumping stroke. The fixed position combs 130 in cooperation with the door 50 trap a known area of the wall portion 132 within the area between the valves 80 and 86. As such, this trapped pumping volume remains constant, regardless of the material being pumped. The fixed position combs 130 are spaced apart longitudinally along the duct F by an amount sufficient to prevent the wall portion 132 from ballooning therebetween. Consequently, when pumping force is applied to the wall portion 132, as will be further explained, then the wall portion 132 will not expand into the area between the fixed combs 130 and thereby alter the pumping volume.

Movable combs 134 extend from pump shoe 82 and are interdigitated with the fixed position combs 130. The movable combs 134 move uniformly linearly through the adjacent spaced fixed combs 130 in order to compress the wall portion 132. Because of the spaced apart cams 92 and 94, then there is little or no tendency for the shoe 82 to cant, with the result that the combs 134 all move by the same amount, in the same unit time, and with equal force for causing substantially constant and uniform compression, and thereby pumping, of the wall portion 132.

Figure 3:
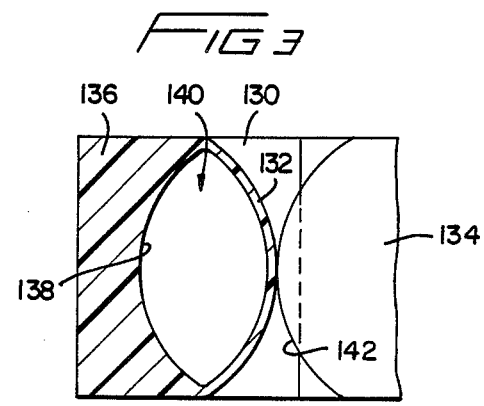
FIG. 3 is a fragmentary cross-sectional view taken along the line 3—3 of FIG. 2 and viewed in the direction of the arrows.
Figure 4:
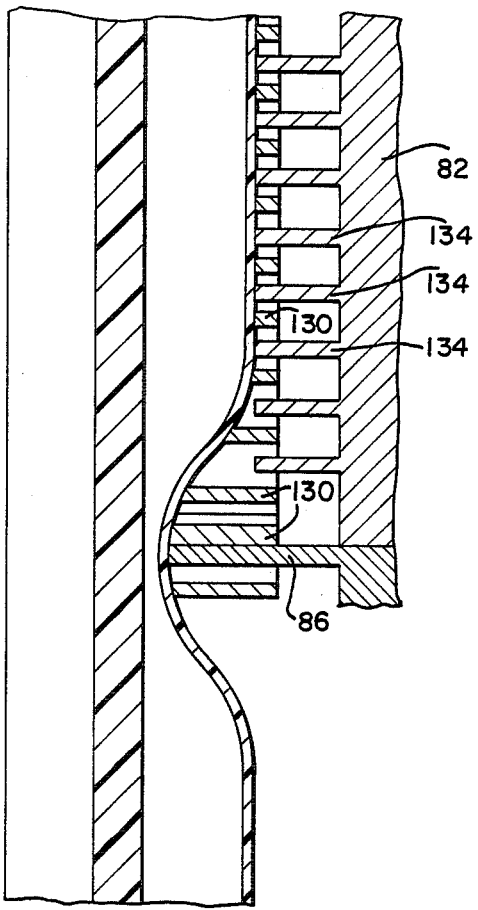
FIGS. 4–5 are fragmentary cross-sectional views illustrating the compression of the medicament delivering tube of FIG. 3 during the pumping cycle.
Figure 4:
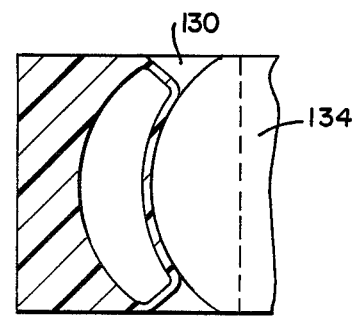
Figure 5:
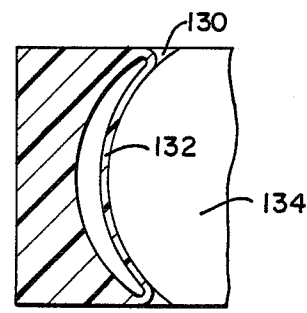

FIGS. 3-5 illustrate the pumping action achieved by the combs 134. Fluid duct F has a base portion 136 of substantial thickness in order to provide strength for the pumping chamber 106 during compression. Base portion 136 has a contoured surface portion 138. Wall portion 132 extends in continuous and uninterrupted manner from the opposite ends of contoured surface 138 to form therewith an oval, or elliptical, fluid duct 140. It can be noted in FIG. 3 that the wall portion 132 is relatively thin in comparison with base portion 136. We have found that the wall portion 132 can be made thinner than would be possible with conventional round tubing because of the additional support provided by base portion 136. Therefore, because the wall portion 132 is thinner, it can then be compressed with less force, thereby conserving energy. Furthermore, the curvature of wall portion 132 is such that there is a tendency to collapse inwardly in a uniform way.

Each of the movable combs 134 has a contact surface 142 which has a contour substantially corresponding to that of the surface 138. In this way, the contact surface 142 causes the wall portion 132 to compress into substantial conformance with surface 138 as the combs 134 move toward the base portion 136. Preferably, the cams 92 and 94 are sized so as to prevent the wall portion 132 from engaging the contoured surface 138, as best shown in FIG. 5, upon the shoe 82 completing its compression stroke. We have found that this slight gap prevents blood cells from being crushed, and thereby destroyed. The pump unit U can therefore be conveniently used for pumping whole blood without fear of damage to the cells.

Figure 10:
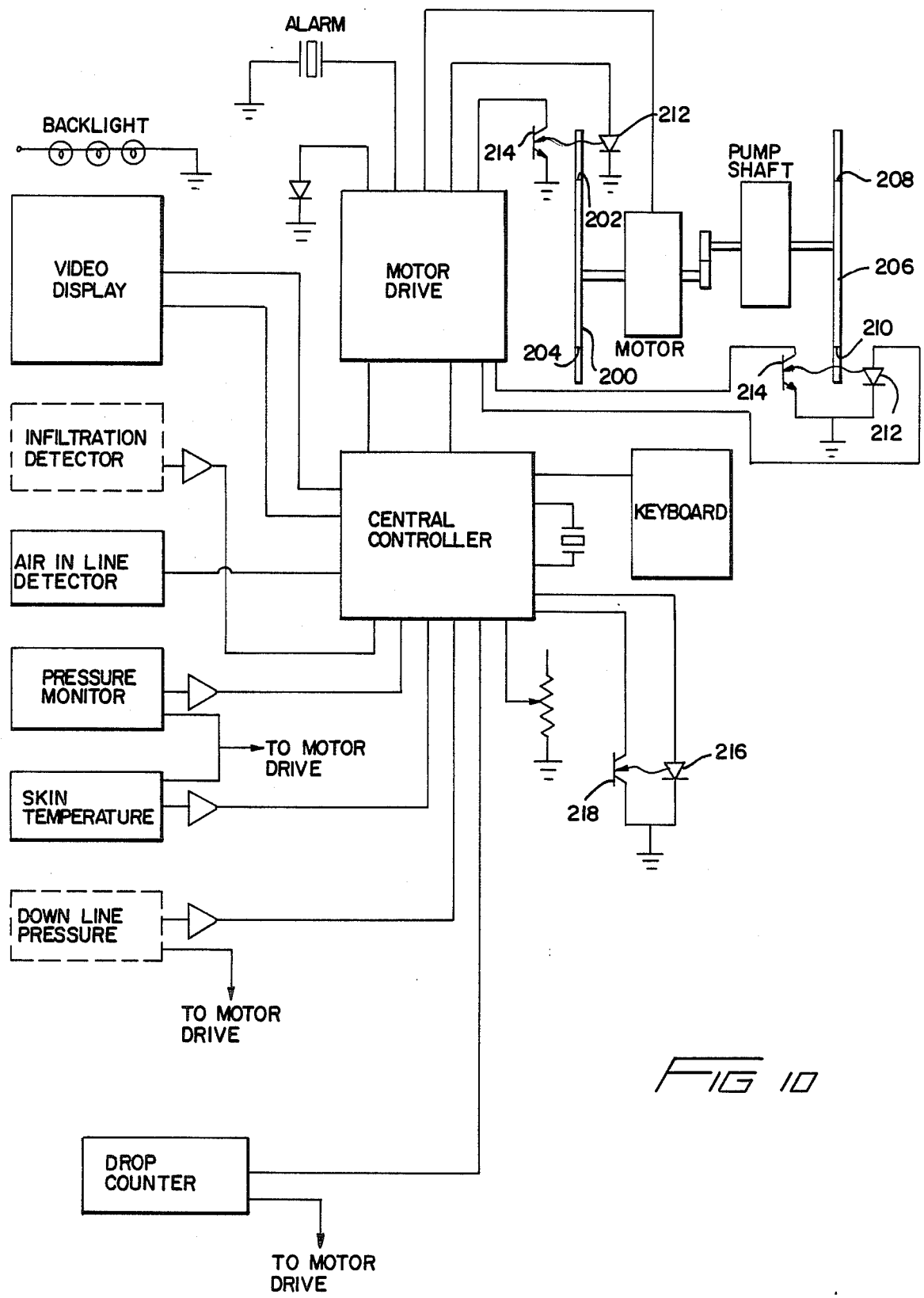

The control schematic for the control unit C is best shown in FIG. 10. A central controller is in electrical connection with a motor drive controller which causes the motor 74 to operate. A disk 200 is carried by the shaft of motor 74 and has a pair of slots 202 and 204. A similar disk 206 is carried by shaft 60 and likewise has slots 208 and 210. The disks 200 and 206 rotate with the associated shafts and are used to provide an indication of rotation of the related components.

A radiation emitter 212, which includes the well known LED, illuminates a radiation detector 214 upon one of the slots being appropriately aligned. Naturally, during rotation, then the disks themselves block the radiation and thereby indicate that rotation is occurring. Should the detectors be illuminated, then an indication of a selected rotational amount is provided for the central controller. This rotation indication is used to monitor the pumping per unit time, particularly useful since the pump volume is known.

FIG. 10 also illustrates the connection of the video display with the central controller. The video display may include the well known CRT display, or other similar displays well known to those skilled in the art. The video display cooperates with the key board, as previously described, in order to input operating parameters into the central controller which are used to cause rotation of the motor 74, and thereby linear movement of the shoe 82.

The pump system P may also include an infiltration detector in electrical connection with the central controller. It is well known that infusion patients may suffer a piercing of the vein. Should the vein be pierced, then the medicament flows into the surrounding muscle tissue, rather than into the vein for being carried by the bloodstream.

An air in line detector, a pressure monitor, a skin temperature monitor and a down line pressure monitor are also in circuit connection with the central controller. The pressure monitor is, preferably, based upon the capacitance principle. The skin temperature monitor is used to measure infusion shock, while the down line pressure monitor looks at the vein pressure.

A drop counter, based upon the above described radiation emission and detection principle, is applied to the drip chamber 104. Naturally, it should be obvious that a given number of drops per unit time are required to supply the appropriate quantity of fluid.

A door latch detector is provided by radiation emission source 216 which illuminates detector 218. In this way, the central controller can be assured that the door 50 of each pump unit U is closed, and thereby secured, so that operation can continue.

FIG. 10 also indicates the backlight which is advantageously positioned within the housing 48 to provide illumination so that the operator can monitor the fluid duct F. Also indicated in FIG. 10 is the alarm for the control unit C.

OPERATION

Operation of the infusion pump system P of FIG. 1 is straightforward. A pump unit U is slid into one of the chambers 12 or 14. The tube 24 carrying the medicament is then inserted into the inlet opening 116 of the administration set A. The door 50 is then closed and secured by rotation of handle 122.

The appropriate pump unit U is selected from module 40 by depressing the appropriate push button 42, 44 or 46. The video display 28 then transmits a number of "lead through" prompts requesting that information be input through any one of the keys of keyboard 30. The central controller employs an algorithm which makes certain that the appropriate operating information and parameters are input, and thereby avoids the need for extensive training for a particular infusion system. The central controller algorithm makes sure that adequate information is received to permit proper operation, and then monitors operation of the infusion pump system P to make sure that those parameters are maintained.

The pumping volume defined by the fixed shoes 130 is known and is constant. Therefore, rotation of the shaft 60 assures that a known quantity of fluid is pumped to the patient through cannula 128. It should be obvious that a given number of strokes per unit time will be required to pump a selected quantity of medicament in like unit time. Preferably, the pumping volume defined by the fixed combs 130 is 0.002 ml. The central controller permits the operator to select a given volume per unit time from between 0.1 to about 2000 ml/hr. Furthermore, the pump system P can be programmed for a specific volume of medicament at predetermined times over an extended period.

As noted, the pump system P is, preferably, battery powered and has sufficient battery life for 1,000 hours at a medicament rate of 125 ml/hr. This extended battery life is attained because of the ability to turn the motor 74 off when pumping is not required. The ratchet pawl 70 prevents the shaft 60 from counterrotating and acts as a brake for maintaining the pump shoe 82 in a fixed position relative to the fluid duct F. Because the motor can be turned to the off position, then battery life is maintained and, just as importantly, pumped medicament can not flow backwardly into the pumping volume during the off stroke. Although a ratchet pawl 70 is disclosed, those skilled in the art will understand that further positive brake apparatus are known, it merely being required that the pump shoe 82 remain in a fixed position without requiring external power.

The pump unit U is particularly advantageous with viscous solutions because of the purge effect which can be achieved. The fluid duct F is vertically disposed within the housing 48 so that the inlet opening 112 is disposed above the outlet opening 126. Any air which may become entrained in the fluid which flows into the pumping chamber 106 will have a tendency to rise upwardly toward duct 110. During the initial stage of the pumping stroke, as known from linear displacement of the shoe 82, then the valve 78 may remain slightly open, as shown in FIGS. 8 and 9, from the fully compressed state of FIG. 2, thereby permitting any entrained air to be pumped upwardly into the drip chamber 106. Naturally, the valve 78 will be fully closed for the majority of the pumping stroke so that the pumping volume can remain fixed.

The pumping cycle is such that the valve 84 closes while the pump shoe 82 retracts upon achieving full compression. The valve 78 simultaneously begins to open in order to permit the generated vacuum to pull fluid from the drip chamber 104 into the pumping chamber 106. At the selected time, then the valve orientation reverses and the shoe 82 begins to move linearly toward door 50, to therefore force the fluid within the pump chamber 106 to be expelled through the outlet 126. This pumping is very efficient because of the relative thinness of the wall portion 132 of the fluid duct F. Because of this relative thinness, then the compression occurs easily without requiring excessive force.

While this invention has been described as having a preferred design, it is understood that it is capable of further modifications, uses and/or adaptations of the invention, following in general the principle of the invention, and including such departures from the present disclosure as come within known or customary practice in the art to which the invention pertains, and as may be applied to the central features hereinbefore set forth, and fall within the scope of the invention of the limits of the appended claims.

What we claim is:

1. An infusion system operable on a resilient longitudinal tube for pumping fluid therethrough, comprising:
   (a) a plurality of fixed spaced apart first comb means for receiving a tube and defining a pumping volume;
   (b) means positioned adjacent to and cooperating with said first comb means for maintaining the tube in position;
   (c) a plurality of movable spaced apart second comb means interdigitated with said first comb means and engageable with the tube for reciprocatingly compressing the pumping volume;
   (d) first and second spaced apart cooperating valve means engageable with the tube for selectively compressing the tube and thereby permitting fluid to flow from or into the pumping volume;
   (e) drive means operably associated with said second comb means and with said first and second valve means for simultaneously reciprocating said second comb means and operating for selectively said first and second valve means; and,
   (f) brake means operably associated with said drive means for preventing unintended reciprocation of said second comb means.

2. An infusion system as in claim 1, wherein:

(a) said second comb means being integral and providing a pump shoe assuring simultaneous uniform reciprocation of said second comb means.

3. An infusion system as in claim 2, wherein:
(a) each of said valve means being disposed adjacent an end one of said first comb means;
(b) each one of said second comb means being disposed between two of said first comb means;
(c) said second comb means having corresponding contoured edges for engagement with the tube; and,
(d) each of said first comb means encompassing the tube.

4. An infusion system as in claim 2, wherein:
(a) rotatable cam means being operably associated with said drive means and with said first and second valve means and with said pump shoe for causing reciprocation of said pump shoe and operation of said valve means; and,
(b) each of said first and second valve means and said pump shoe having a rotatable cam follower cooperatively engaged with said cam means.

5. An infusion system as in claim 4, wherein:
(a) said cam means including first, second, third and fourth cams, said first cam being associated with said first valve means, said second and third cams being associated with said pump shoe and said fourth cam being associated with said second valve means;
(b) said second and third cams being spaced apart and disposed proximate opposite ends of said pump shoe for assuring uniform reciprocation of said pump shoe; and,
(c) said cams being coaxial and mounted to a common rotatable shaft.

6. An infusion system as in claim 5, wherein:
(a) said drive means including a motor having a rotatable shaft caring a first gear;
(b) a second gear being carried by said common shaft and being meshingly engaged with said first gear so that rotation of said motor shaft causes cooperative rotation of said common shaft; and,
(c) control means being operably connected with said motor for energizing said motor for a selected period and for deenergizing said motor for another selected period and said brake means preventing rotation of said common shaft during said another selected period.

7. An infusion system as in claim 6, wherein:
(a) said brake means including a ratchet assembly engaged with said second gear means for permitting rotation thereof in one direction only.

8. An infusion system as in claim 6, wherein:
(a) said control means including first means operably associated with said common shaft for monitoring rotation thereof and second means operably associated with said motor shaft for monitoring rotation thereof; and,
(b) said first and second monitoring means each including a slotted disk, a light source and a light detector so that rotation of said disks causes light to be sequentially detected by said detectors for thereby indicating rotation of the shafts.

9. An infusion system as in claim 6, wherein:
(a) battery means operatively connected with said control means and with said motor for providing electric power thereto.

10. An infusion pump, comprising:
(a) a housing with a pivotal door means connected thereto;
(b) a plurality of fixed spaced apart first comb means positioned within said housing and directed toward said door means and defining a pumping volume;
(c) a plurality of spaced apart second comb means interdigitated with said first comb means and each second comb means movable toward and away from said door means and said second comb means being integral and providing a pump shoe;
(d) a resilient tube engaged with said first comb means in cooperation with said door means;
(e) first and second spaced apart cooperating valve means engageable with said tube for selectively compressing said tube and thereby permitting fluid to selectively flow into or from said pumping volume;
(f) drive means operably associated with said second comb means and with said first and second valve means for selectively simultaneously reciprocating said second comb means and operating said first and second valve means; and,
(g) brake means operably associated with said drive means for preventing unintended reciprocation of said second comb means.

11. An infusion pump as in claim 10, wherein:
(a) third valve means being operably associated with said tube for controlling fluid flow to said pumping volume;
(b) a first handle portion of said third valve means extending through said door for permitting adjustment of said third valve means; and,
(c) a second handle portion engageable with said housing for maintaining said door secured.

12. An infusion pump as in claim 11, wherein:
(a) said third valve means including a drip chamber upstream of said pumping volume;
(b) inlet supply means being in operative connection with said drip chamber for connection with a fluid source; and,
(c) said tube being integral with said third valve means and said drip chamber.

13. An infusion pump as in claim 10, wherein:
(a) said tube comprised of an elastomeric material and having a support portion of substantial thickness and an overlying portion; and,
(b) said support portion having a curvilinear surface and said overlying portion being correspondingly curvilinear and therewith forming a substantially eliptical fluid aperture so that the curvilinear portions are substantially contiguous when said tube is compressed.

14. An infusion pump as in claim 13, wherein:
(a) each of said second comb means having a contact surface contoured in substantial conformity with said curvilinear surface; and,
(b) means preventing said second comb means from compressing said overlying portion into contiguous engagement with said curvilinear surface.

15. An infusion pump as in claim 10, wherein:
(a) said drive means including rotary means and rotary to linear conversion means for moving said second comb means linearly; and,
(b) said brake means being operatively engaged with said rotary means for permitting rotation thereof in one direction only.

16. An infusion pump as in claim 15, wherein:

(a) said rotary means including a motor having a first rotatable shaft carrying a first gear; and, (b) said conversion means including a second rotatable shaft carrying a second gear meshingly engaged with said first gear and a plurality of cams, each of said cams being associated with one of said first and second valve means and said second comb means.

17. An infusion pump as in claim 16, wherein:

(a) said brake means including a ratchet assembly operably engageable with one of said first and second gears;

(b) said second comb means being integral and providing a pump shoe; and, (c) at least two spaced apart cams being engageable with said shoe for assuring linear movement thereof.

18. An infusion pump as in claim 12, wherein:

(a) said tube being vertically disposed so that said drip chamber is at a higher elevation than is the outlet of said pumping volume;

(b) said door having a transparent portion; and, (c) a recess in said door for seating said tube.

19. An infusion system as in claim 15, wherein:

(a) means being operably associated with said rotary means for monitoring rotation thereof and including a slotted disk rotatable with said rotary means, a radiation emitter and a radiation detector.

* * * * *